(12) United States Patent
Kuhnemund et al.

(10) Patent No.: US 12,377,412 B2
(45) Date of Patent: Aug. 5, 2025

(54) SAMPLE ANALYSIS DEVICE

(71) Applicant: COUNTAGEN AB, Stockholm (SE)

(72) Inventors: Malte Kuhnemund, Solna (SE); Ivan Hernandez-Neuta, Stockholm (SE); Felix Neumann, Stockholm (SE)

(73) Assignee: COUNTAGEN AB, Stockholm (SE)

( * ) Notice: Subject to any disclaimer, the term of this patent is extended or adjusted under 35 U.S.C. 154(b) by 913 days.

(21) Appl. No.: 17/602,161

(22) PCT Filed: Apr. 16, 2020

(86) PCT No.: PCT/EP2020/060771
§ 371 (c)(1),
(2) Date: Oct. 7, 2021

(87) PCT Pub. No.: WO2020/212531
PCT Pub. Date: Oct. 22, 2020

(65) Prior Publication Data
US 2022/0193662 A1 Jun. 23, 2022

(30) Foreign Application Priority Data
Apr. 16, 2019 (SE) .................... 1930131-6

(51) Int. Cl.
*B01L 3/00* (2006.01)
*C12N 15/10* (2006.01)

(52) U.S. Cl.
CPC ...... *B01L 3/50255* (2013.01); *C12N 15/1017* (2013.01); *B01L 2200/0668* (2013.01); *B01L 2300/0663* (2013.01); *B01L 2300/0681* (2013.01); *B01L 2300/069* (2013.01); *B01L 2300/0829* (2013.01); *B01L 2300/0887* (2013.01); *B01L 2300/165* (2013.01); *B01L 2400/0406* (2013.01)

(58) Field of Classification Search
None
See application file for complete search history.

(56) References Cited

U.S. PATENT DOCUMENTS

| | | |
|---|---|---|
| 10,208,336 B2 | 2/2019 | Ohman |
| 2009/0298191 A1 | 12/2009 | Whitesides |
| 2012/0231466 A1 | 9/2012 | Kelso |
| 2013/0078711 A1 | 3/2013 | Chen |
| 2017/0022548 A1 | 1/2017 | Ohman |
| 2018/0119201 A1* | 5/2018 | Howell ............... G01N 33/586 |

FOREIGN PATENT DOCUMENTS

| | | |
|---|---|---|
| EP | 3350342 | 2/2020 |
| EP | 3532636 | 3/2021 |
| WO | WO 2016/174649 | 11/2016 |
| WO | WO 2018/078469 | 5/2018 |
| WO | WO 2018/128585 | 7/2018 |

OTHER PUBLICATIONS

Ciftci et al. 2020 "Digital Rolling Circle Amplification-Based Detection of Ebola and Other Tropical Viruses", The journal of Molecular Diagnostics, vol. 22, No. 2, 2020.
Hernández-Neuta, I. (Oct. 12, 2017) "Nucleic Acid Analysis Tools—Novel Technologies and Biomedical Applications", (doctoral dissertation). Department of Biochemistry and Biophysics, Stockholm University.
Ciftci S. (May 15, 2019) "Padlock Probe-based Nucleic Acid Amplification Tests—Point-of-care Diagnostics of Infectious Diseases", (doctoral dissertation). Department of Biochemistry and Biophysics, Stockholm University.
Ciftci et al. 2019 "A Novel Mutation Tolerant Padlock Probe Design for Multiplexed Detection of Hypervariable RNA Viruses", Scientific Reports, vol. 9, 2872.
PCT International Search Report and Written Opinion for PCT/EP2020/060771 dated Jul. 10, 2020 (11 pages).
Kuhnemund et al., "Sensitive and Inexpensive Digital DNA Analysis by Microfluidic Enrichment of Rolling Circle Amplified Single-Molecules", *Nucleic Acids Research*, 2017, 45(8).

* cited by examiner

*Primary Examiner* — Katherine D Salmon
(74) *Attorney, Agent, or Firm* — Mueting Raasch Group

(57) ABSTRACT

A sample analysis device (9) comprises a sample receiving well (7) configured to receive a liquid sample (4) comprising rolling circle amplification products (RCPs) (5). The device (9) also comprises a filter membrane (1) permeable for liquid of the liquid sample (4) but substantially impermeable for RCPs (5) in the liquid sample (4). The sample receiving well (7) is defined in the filter membrane (1) or is in connection with the filter membrane (1). An absorption layer (3) is in liquid connection with the filter membrane (1) and is configured to suck liquid from the liquid sample (4) received in the sample receiving well (7) through the filter membrane (1) by capillary force. The dimensions of the sample receiving well (7) are restricted to a field of view of an optical sensing device (10).

7 Claims, 7 Drawing Sheets

Specification includes a Sequence Listing.

SAMPLE ANALYSIS DEVICE

This application is a U.S. National Stage Application of International Application No. PCT/EP2020/060771 filed Apr. 16, 2020, which was published in English on Oct. 22, 2020, as International Publication No. WO 2020/212531 A1. International Application No. PCT/EP2020/060771 claims priority to Swedish Patent Application No. 1930131-6 filed Apr. 16, 2019.

SEQUENCE LISTING

This application contains a Sequence Listing electronically submitted via EFS-Web to the United States Patent and Trademark Office as an ASCII text file entitled "2021 Oct. 7-SeqListing_ST25.txt" having a size of 2 kilobytes and created on Oct. 7, 2021. The information contained in the Sequence Listing is incorporated by reference herein.

TECHNICAL FIELD

The present invention generally relates to a sample analysis device, and in particular to such a sample analysis device for measurements of rolling circle amplification (RCA) products (RCPs).

BACKGROUND

The detection and accurate quantification of biomolecules, such as proteins and nucleic acids, is of importance for biomedical research and clinical diagnostics. Identifying and determining the number of specific biomarkers can help to determine differences in function of different molecules, cells, tissues, and whole organisms and help to distinguish healthy from disease state. Single molecule detection methods have proven superior to methods that measure the bulk signal, by being able to measure subtle differences in concentration of molecules where bulk measurements would not detect a difference.

Rolling circle amplification (RCA) is a useful single molecule amplification technique that can be used to amplify and, thus, increase the size of individual small molecules and make them detectable for an optical sensor. Rolling circle amplified single molecules can be labeled with a range of different optical labels, such as fluorophores, which make them visible to a fluorescent detector. However, quantifying RCA products (RCPs) from a liquid sample containing RCPs can be challenging. While the absolute numbers of RCPs in a sample may be sufficiently high to detect and measure the difference between target molecules with statistical robustness, the concentration of RCPs in the sample may be quite low, which might require that the entire sample volume has to be analyzed in order to detect all, or a substantial fraction of all RPCs in the liquid sample.

RCPs in a liquid sample can be applied and spread onto a 2-dimensional (2D) surface, such as a glass slide, and the total number of RCPs can then be determined by imaging the entire glass slide. Such a procedure, however, requires a sophisticated automated microscope with scanning stage that acquires images of several adjacent fields of view of the microscope optical objective with high precision so that the entire area can be captured.

The use of filtration of RCPs onto a porous membrane can be used to up-concentrate RCPs by reducing the sample volume, while maintaining the number of RCPs thereby effectively increasing the concentration of RCPs on the porous membrane onto which the RCPs are filtered as disclosed in U.S. Pat. No. 10,208,336. However, application of the RCPs onto a porous filter as taught in U.S. Pat. No. 10,208,336 result in RCPs being spread over a large area that will still require sophisticated imaging tools to analyze the entire area with many fields of view of a microscope objective. In fact, 9×9 images are needed to cover the whole area.

Kühnemund et al., Sensitive and inexpensive digital DNA analysis by microfluidic enrichment of rolling circle amplified single-molecules, *Nucleic Acids Research* (2017), 45(8): e59 discloses a multi-layer hybrid microfluidic chip that focuses RCPs onto a small defined area using active force in the form of a pump system. The RCPs are thereby concentrated onto an area of a single field of view of a microscope objective. However, the pump system required for the operation makes the multi-layer hybrid microfluidic chip complicated in everyday use. Moreover, the manufacture of such active force multi-layer hybrid microfluidic chip is complex and expensive.

SUMMARY

It is a general objective to enable passive concentration and focus of RCPs from a liquid sample onto a small defined area.

This and other objectives are met by embodiments as disclosed herein.

The present invention is defined in the independent claims. Further embodiments are defined in the dependent claims.

A sample analysis device is described herein that enables RCA products from a liquid sample to be focused onto a small defined area that corresponds to the area of a single field of view of an optical sensing device, such as a microscope objective. The sample analysis device facilitates analysis of samples containing RCA products with simple optical read-out, while still achieving a high detection sensitivity.

BRIEF DESCRIPTION OF THE DRAWINGS

The embodiments, together with further objectives and advantages thereof, may best be understood by making reference to the following description taken together with the accompanying drawings, in which.

Figure 1:
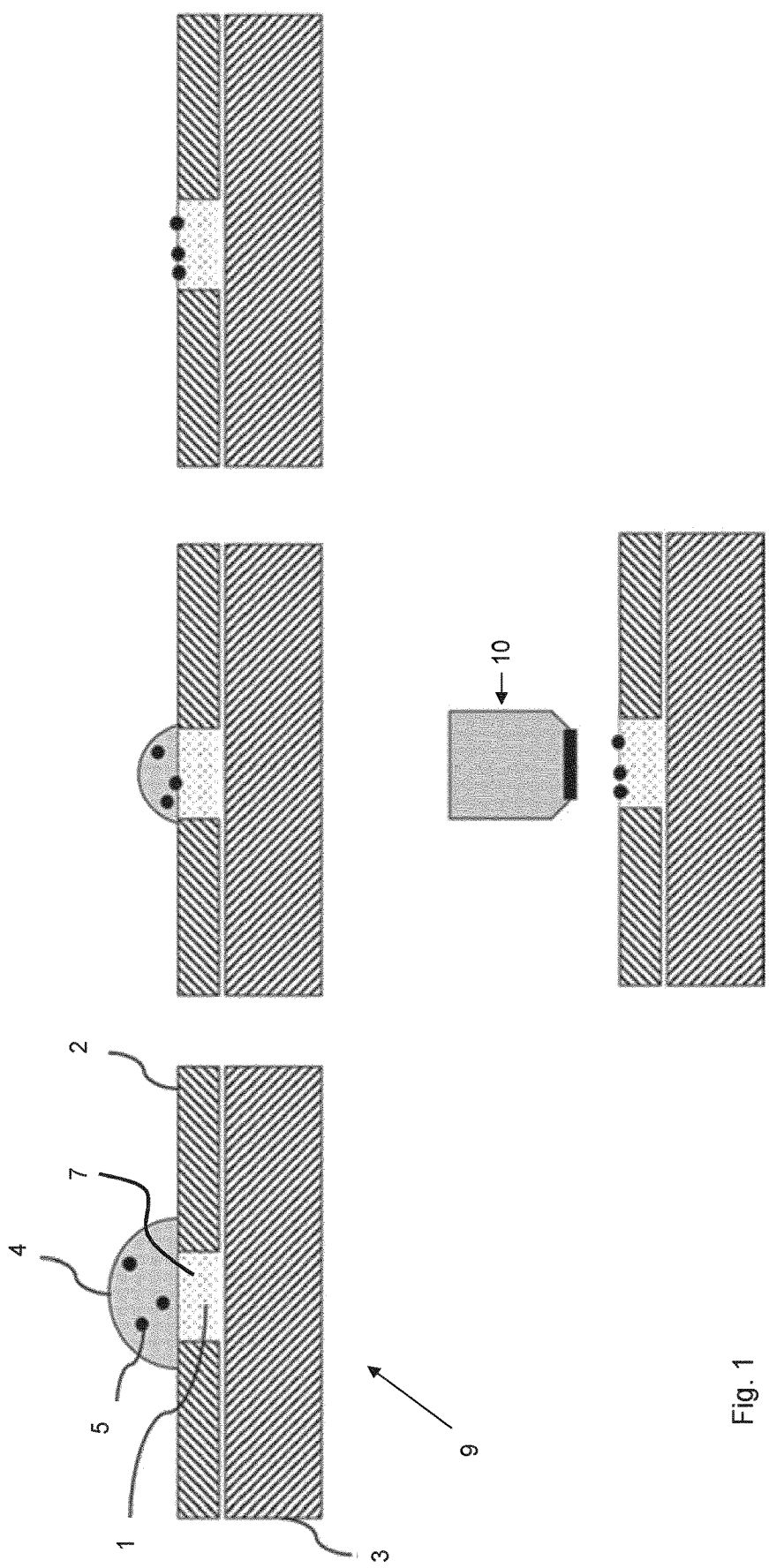
FIG. 1. Side views of a cross section of an embodiment of the sample analysis device illustrating the main operations of the sample analysis device.

In the figures, the following reference numbers have been used:
1. Filter membrane;
2. Fluid-impermeable barriers, also referred to as hydrophobic barriers;
3. Absorption layer;
4. Liquid sample containing RCPs;
5. RCPs;
6. Spacer layer;
7. Sample receiving well;
8. Liquid-impermeable layer;
9. Sample analysis device;
10. Optical sensing device;
11. Through hole through liquid-impermeable layer; and
12. Through hole through space layer.
13. Support layer

DETAILED DESCRIPTION

Throughout the drawings, the same reference numbers are used for similar or corresponding elements.

The present invention generally relates to a sample analysis device, and in particular to such a sample analysis device for measurements of rolling circle amplification (RCA) products (RCPs).

A sample analysis device for quantification of target molecules, amplified by RCA, contained in a liquid is presented. The sample analysis device is comprised of a filter membrane, preferably a porous hydrophilic membrane, and a well-defined sample receiving well. The porous membrane is in close contact with a porous absorbing layer of an absorbent material that promotes a vertical flow of the liquid through the porous membrane within the boundaries of the sample receiving well. Rolling circle amplified molecules, denoted rolling circle amplification products (RCPs) herein, contained in the liquid are, thus, immobilized in and/or on the portion of the porous membrane corresponding to the sample receiving well. The area of the sample receiving well corresponds to a single field of view of an optical sensing device. The sample analysis device can be used to enrich RCPs from a liquid containing a low concentration of such molecules onto the sensor detection zone so that detection of the molecules requires only a single measurement that detects all molecules contained in the liquid sample and thereby avoids the need to measure at several different areas on the field of detection and avoids using sophisticated imaging tools.

The sample analysis device is in particular designed to analyze and quantify molecules amplified by rolling circle amplification. The sample analysis device is designed to define a sample receiving well within or in connection with a porous membrane where rolling circle amplified molecules contained in a liquid sample are immobilized for simplified analysis and improved sensitivity. The sample analysis device is also comprised of an absorbing or absorbent layer(s) that is placed underneath and in close contact with the porous membrane so that applied liquids containing rolling circle amplified molecules are sucked or wicked through the porous membrane promoting a vertical flow of the liquid by capillary force. Rolling circle amplified molecules are, thus, filtered and immobilized on the surface of and/or within the porous membrane and within the boundaries of the sample receiving well. Dimensions of the sample receiving well are restricted so that the total number of rolling circle amplified products contained in the liquid sample can be captured and, thus, detected within the area of a single sensor's field of detection. Such a sample analysis device simplifies methods for quantification and analysis of rolling circle amplified molecules.

Figure 3:
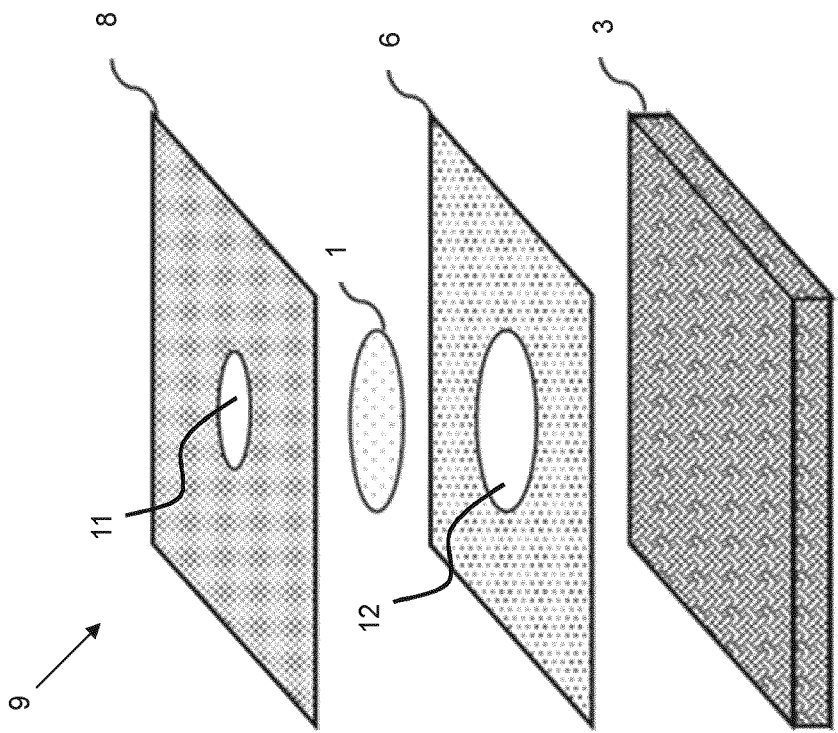
FIG. 3. Exploded view of an embodiment of the sample analysis device, in which the sample receiving well is defined by a liquid-impermeable layer.
Figure 2:
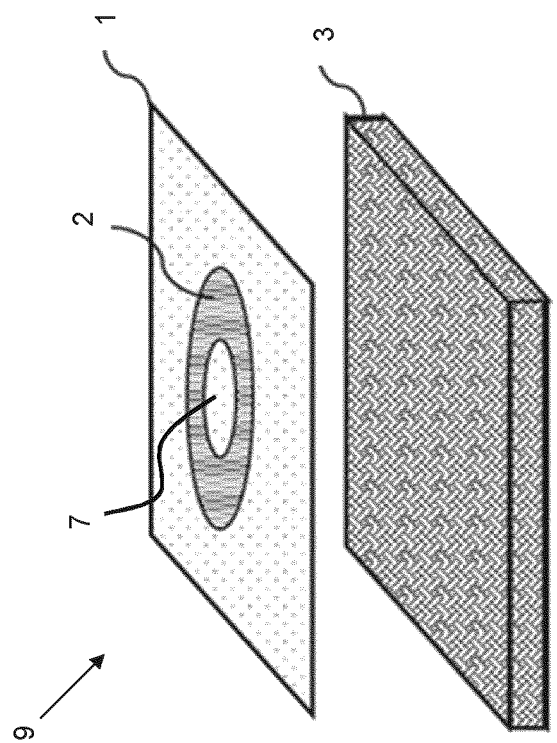
FIG. 2. Exploded view of an embodiment of the sample analysis device, in which the sample receiving well is defined by hydrophobic barriers that permeate the thickness of the filter membrane.

With reference to FIGS. 1 to 3, the sample analysis device 9 comprises a sample receiving well 7 configured to receive a liquid sample 4 comprising RCPs 5. The sample analysis device 9 also comprises a filter membrane 1 permeable for liquid of the liquid sample 4 but substantially impermeable for RCPs 5 in the liquid sample 4. The sample receiving well 7 is defined by a hydrophobic barrier 2 within the filter membrane 1 (see FIGS. 1 and 2), or by an additional liquid-impermeable layer 8 on top of the filter membrane 1 (see FIG. 3). The sample analysis device 9 further comprises an absorption layer 3 in liquid connection or communication with the filter membrane 1. The absorption layer 3 is configured to suck liquid from the liquid sample 4 received in the sample receiving well 7 through the filter membrane 1 by capillary force. According to the embodiments, dimensions of the sample receiving well 7 are restricted to a field of view of an optical sensing device 10.

In an embodiment, the sample analysis device 9 comprises multiple, i.e., at least two, absorption layers 3. These multiple absorption layers 3 could then be arranged in a stack, i.e., arranged on each other. The absorption layers 3 in the stack could then be similar absorption layers 3, such as having a same thickness and being made of the same material. Alternatively, different absorption layers 3 could be included in the stack. The different absorption layers may increase the liquid absorbing capacity of the disclosed sample analysis device.

In an embodiment, the sample analysis device 9 comprises multiple filter membranes 1. These multiple filter membranes 1 could be then be arranged in a stack (e.g. an array). The filter membranes 1 in the stack (e.g. the array) could then be similar filter membranes 1, such as having a same thickness, having a same average pore diameter and being made of the same material. Alternatively, different filter membranes 1 could be included in the stack (e.g. the array).

In an embodiment, the boundaries of the sample receiving well(s) is/are liquid-impermeable.

In an embodiment, the filter membrane 1 is a hydrophilic filter membrane 1 that comprises hydrophobic barriers 2 extending through a thickness of the filter membrane 1. The hydrophobic barriers 2 define the sample receiving well 7 in the filter membrane 1.

The hydrophobic barriers 2 are, in an embodiment, printed in the hydrophilic filter membrane 1. For instance, solid wax, paraffin or any other hydrophobic material could be printed in the hydrophilic filter membrane 1. The solid printed pattern of the hydrophobic material is preferably heated so that the hydrophobic material is melted and penetrates through the thickness of the hydrophilic filter membrane 1. After cooling, such as to room temperature, the hydrophobic material is solidified in the hydrophilic membrane 1 and forms the hydrophobic barriers 2.

Another technique of forming the hydrophobic barriers 2 is to use a printing device that melts the hydrophobic material during the printing process and then allows the printed and melted material to solidify into the hydrophobic barriers 2.

In a particular embodiment, the sample analysis device 9 comprises multiple sample receiving wells 7. In such a particular embodiment, the sample analysis device 9 preferably comprises one filter membrane 1 or one stack (e.g. an array) of multiple filter membranes 1. The sample analysis device 9 also comprises one absorption layer 3 or one stack of multiple absorption layers 3. The multiple sample receiving wells 7 are then defined in the filter membrane 1 or in the stack of multiple (e.g. the individual array of) filter membranes 1.

In an embodiment, the sample analysis device 9 comprises a liquid-impermeable layer 8 connected to the filter membrane 1 and comprising a through hole 11 forming the sample receiving well 7.

In a particular embodiment, the liquid-impermeable layer 8 comprises multiple through holes 11 forming multiple sample receiving wells 7. In this particular embodiment, the sample analysis device 9 preferably comprises multiple filter membranes 1, preferably one such filter membrane 1 per sample receiving well. The sample analysis device 9 preferably also comprises one absorption layer 3. In another embodiment, the sample analysis device 9 comprises a single filter membrane 1 or a single stack of multiple filter membranes 1 (e.g. an array of multiple filter membranes) that is/are connected to the liquid-impermeable layer 8 with multiple through holes 11. In such an embodiment, liquid in the liquid sample 4 may spread laterally in the filter membrane 1. However, the RCPs 5 present in the liquid sample 4 will be trapped, such as absorbed, onto and/or into the filter membrane 1 and will not spread laterally.

In an embodiment, the sample analysis device 9 may optionally comprise a spacer layer 6 sandwiched between the liquid-impermeable layer 8 and the absorption layer 3. The spacer layer 6 comprises a through hole 12 configured to house the filter membrane 1.

In an embodiment, the sample analysis device 9 may have a length that ranges from about 10 mm to 200 mm, such as from about 10 mm to 150 mm, for example from about 10 mm to about 100 mm.

In an embodiment, the sample analysis device 9 may have a width that ranges from about 10 mm to 200 mm, such as from about 10 mm to 150 mm, for example from about 10 mm to about 100 mm, or from about 10 mm to about 80 mm, or for example from about 15 mm to about 70 mm.

In an embodiment, the spacer layer 6 is made of made of a thermoplastic material. In a particular embodiment, the thermoplastic material is selected from the group consisting of polyethylene terephthalate, polycarbonate, cyclo-olefin polymers, poly(methylmetacrylate), polypropylene, polytetrafluroethylene, polyethersulfone, and a combination thereof.

In an embodiment, the spacer layer 6 is preferably liquid-impermeable.

In an embodiment, the sample analysis device 9 may comprise a support layer 13 attached to a bottom surface of the absorbent layer 3. This support layer provides structural support and rigidity to the sample analysis device 9. The support layer is preferably in the form of a plastic layer. Although, the support layer may take other forms.

In an embodiment, the filter membrane 1 is made of a material selected from the group consisting of nitrocellulose, nitrocellulose mixed esters, nylon, polyvinylidene fluoride, polyethersulfone, polyether, polycarbonate and aluminum oxide.

In an embodiment, the filter membrane 1 has a thickness of from about 0.01 µm to about 100 µm, such as from about 0.05 µm to 0.5 µm, for example from about 0.07 µm to about 0.2 µm, or wherein the filter membrane has a thickness of about 0.1 µm.

In an embodiment, the filter membrane 1 has a surface area of from about 2 to about 20 mm$^2$, such as from about 5 to about 15 mm$^2$, for example from about 5 to about 10 mm$^2$.

In an embodiment, the filter membrane 1 is substantially circular in shape, such as circular in shape, wherein the filter membrane has a diameter in the range of from about 0.1 to about 10 mm, such as from about 0.5 mm to about 10 mm, for example from about 1 mm to about 5 mm, or from about 1 mm to about 3 mm, or wherein the filter membrane is circular having a diameter of about 2 mm.

In an embodiment, the filter membrane 1 is in the form of a porous membrane 1, preferably a porous hydrophilic membrane 1.

In an embodiment, the absorption layer 3 is made of fibers that can form a porous structure or are otherwise arranged so that they promote capillarity. In a particular embodiment, the absorption layer 3 is therefore a porous absorption layer.

In an embodiment, the absorption layer 3 is made of a material selected from the group consisting of cellulose, glass fiber, cotton, polyester, polyurethane, and a combination thereof.

In an embodiment, the absorption layer 3 is configured to suck liquid from the liquid sample 4 received in the sample receiving well 7 through the filter membrane 1 by capillary force and retain the liquid within the absorption layer 3.

In an embodiment, an area of the sample receiving well 7 is equal to or smaller than the field of view of the optical sensing device 10.

In an embodiment, the sample receiving well 7 has a diameter selected within a range of from 0.5 µm to 9 mm, preferably within a range of from 0.5 µm to 5 mm, such as from about 1 mm to about 5 mm, or from about 1 mm to about 3 mm, for example about 1 mm, about 1.5 mm, about 2 mm, about 2.5 mm, or about 3 mm.

Figure 6:
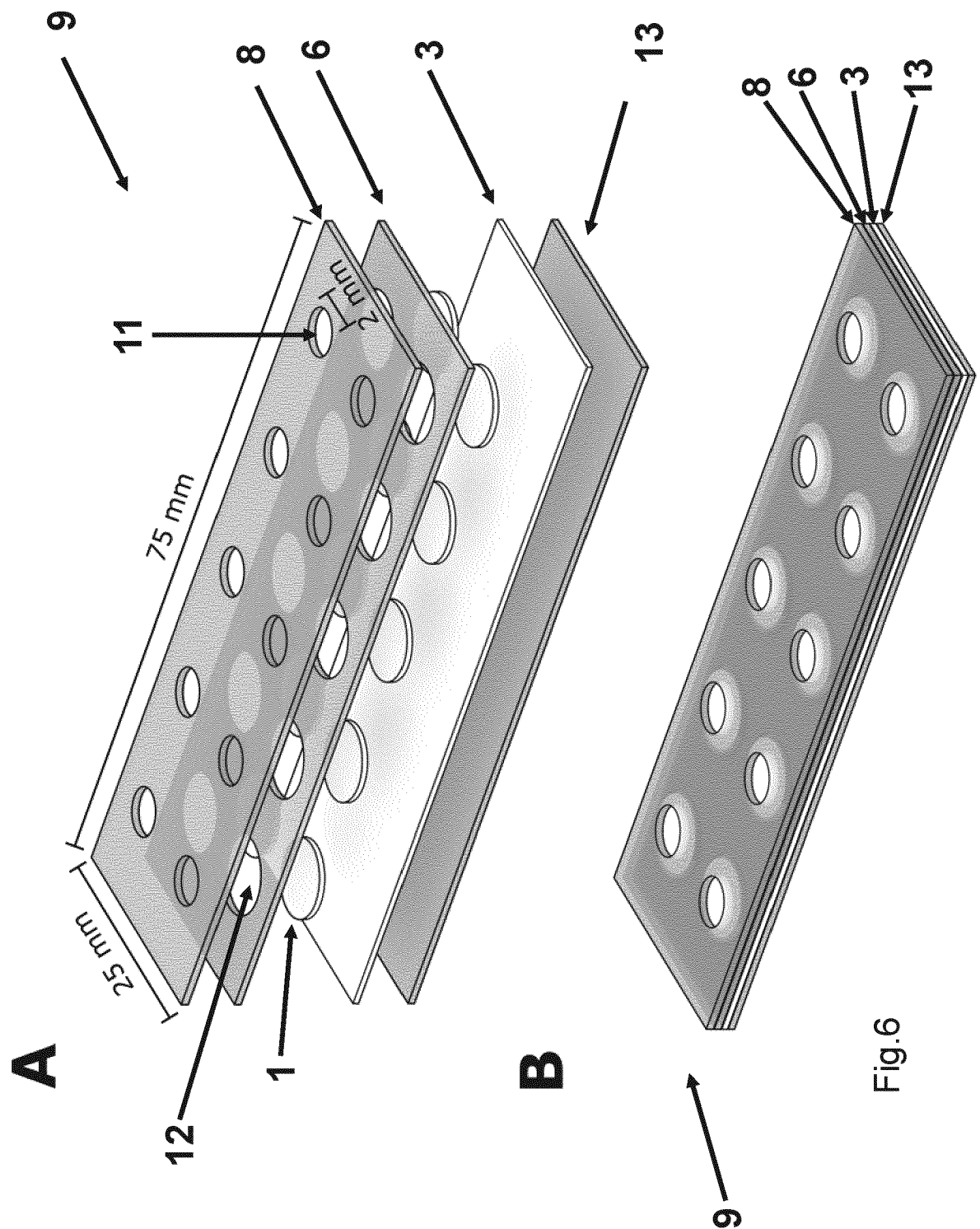
FIG. 6. A. Exploded view of an embodiment of an exemplary format of the sample analysis device with multiple sample receiving wells. B. The same embodiment as depicted in 6A., but wherein the layers of the device are fit together.

FIG. 6 details an exemplary sample analysis device 9 according to the invention with ten arrayed sample receiving wells. The device has the dimensions of a microscopy slide and allows for quantification of RCPs in all the sample receiving wells with single microscope images. FIG. 6 A shows an exploded view of the exemplary sample analysis device comprising a liquid impermeable layer 8 on top of a spacer layer 6.

The spacer layer 6 comprises ten arrayed through holes 12 configured to each individually house a different filter membrane 1.

Positioned below the spacer layer is an absorption layer and at the bottom of the device is a support layer 13. The layers 8, 6 and 13 are in this example made from hard thermoplastic polymers to add support.

FIG. 6B shows a perspective view of the assembled exemplary sample analysis device.

Another aspect of the embodiments relates to a sample analysis system. The sample analysis system comprises an optical sensing device 10 having a field of view and a sample analysis device 9 according to any of the embodiments.

A further aspect of the embodiments relates to a sample analysis method. The method comprises applying a liquid sample 4 comprising RCPs 5 into or onto a sample receiving well 7 of a sample analysis device 9 according to any of the embodiments. The method also comprises filtrating the liquid sample 4 through a filter membrane 1 of the sample analysis device 9 by sucking, by capillary force, liquid from the liquid sample 4 through the filter membrane 1 and into an absorption layer 3 of the sample analysis device 1. The method further comprises determining the amount of RCPs 5 captured in an area of the filter membrane 1 corresponding to the sample receiving well 7 using an optical sensing device 10.

The RCPs 5 can be labelled RCPs 5. In such a case, the amount of RCPs 5 captured in the area of the filter membrane 1 can be optically determined by detection of the labels. Alternatively, RCPs 5 can be first captured on the filter membrane 1 and thereafter labeled in the sample analysis device.

Various labels can be used including fluorophores, colorimetric labels, chemiluminescent labels, phosphorescent labels and particles, such as gold and silver particles.

Different labels can be used for different species of RCPs 5 in the liquid sample 4.

In an embodiment, a liquid mountant or mounting medium can be applied to labeled RCPs 5 immobilized onto and/or into the filter membrane 1 to protect the label from fading during microscopy-based detection.

In an embodiment, a transparent coverslip, such as glass or plastic coverslip, is put onto the sample analysis device 9 prior to determining the amount of RCPs 5 captured in the area of the filter membrane 1.

The liquid in the liquid sample 4 is preferably water or an aqueous solution, such as a buffer solution or a reaction solution.

EXAMPLES

Example 1

Quantification of Serial Dilutions of RCPs

This example demonstrates the analytical capabilities of the sample analysis device.

Sample Analysis Device

A sample analysis device as shown in FIG. 3 was manufactured by Aline (U.S.). The filter membrane was a Protran™ NC Nitrocellulose membrane with a 0.1 µm pore size (GE Healthcare lifesciences), the absorption layer was a cellulose fiber sample pad sheet (Meck-Millipore), the spacing layer was in the form of pressure sensitive adhesive (Aline) and the liquid-impermeable layer was of polyethylene terephthalate (Aline). The sample receiving wells had a diameter of 1.5 mm. The sample analysis device was manufactured to have dimensions of a standard microscope slide 25×75 mm with ten sample receiving wells arrayed over the sample analysis device.

RCPs Production

Initial circular templates for rolling circle amplification were generated by performing a padlock probe ligation reaction templated by a single-stranded DNA synthetic target mimicking that of a conserved 40 bp region of the nuc gene from *Staphylococcus aureus*. The ligation of padlock probes was performed with a mix composed of 10 nM padlock probe ($PO_4$-TGCTTTGTTTCAGGTGTA GTGTATGCAGCTCCTCAGTAATAGTGTCTTAGTCG-GAAGTACTACTCTCTTCTCTACACCTTTTT AGGA, SEQ ID NO: 1), 30 nM synthetic target (TTAAAT-TAATGTACAAAGGTCAACCAATGACATTCAGACT-ATTATTGGTTGATACACCTGAAACAA AGCATCCTAAAAAAGGTGTAGAGA, SEQ ID NO: 2), T4 ligase reaction buffer (66 mM Tris-HCl (pH 7.5), 10 mM DTT, 10 mM $MgCl_2$, Blirt S.A), 0.2 µg/µl BSA, 0.68 mM ATP (Blirt S.A) and 1 U T4 ligase (Blirt S.A) in a final volume of 50 µl. The mixture was incubated at 37° C. for 15 min followed by 65° C. for 2 min. Resulting circles from this reaction were diluted to 10 pM in mQ $H_2O$ and thereafter amplified by a target-primed RCA reaction, for which a mixture comprising 5 pM ligated circles, 0.2 µg/µl BSA, φ29 polymerase reaction buffer (33 mM Tris-acetate pH-7.9, 10 mM Mg-acetate, 66 mM K-acetate, 0.1% (v/v) Tween 20, 1 mM DTT), 125 µM dNTPs (Blirt S.A) and 0.4 U/µl φ29 polymerase (Monserrate) was used to amplify the above-mentioned dilution of circles. The RCA reaction was incubated at 37° C. for 3 h and 65° C. for 2 min.

Labelling of RCPs

1:10 serial dilutions of resulting RCA products were prepared in 1× φ29 polymerase reaction buffer. Dilutions of RCA products were labelled by hybridization of fluorescently tagged oligonucleotides complementary to the repeats within the RCA product. For this, 50 µl RCA product dilutions were mixed with 20 µl of a labelling buffer containing 20 mM Tris-HCl (pH 8.0), 20 mM ethylenediaminetetraacetic acid (EDTA), 0.10% Tween 20, 2 M NaCl and 10 nM of Cyanine 3 (Cy3)-tagged oligonucleotide (Cy3-TCCTCAGTAATAGTCTCTTACTTTT, SEQ ID NO: 3). The hybridization reaction was incubated for 2 min at 75° C. and 15 min at 55° C.

RCPs Concentration Determination

To estimate the resulting concentration of RCPs, 10 µl of the hybridization reaction (highest concentration) were put on a Superfrost slide (ThermoFisher) and spread on the surface using a 24×24 mm Menzel Gläser coverslip (VWR). The slide was incubated at room temperature for 15 min to allow the RCPs to attach to the slide. After incubation, five fields of view within the 24×24 mm coverslip were imaged with a Zeiss Axio Imager Z2 epifluorescence microscope with a 20× magnification objective with a field of view of 0.75×0.75 µm. Resulting RCPs were quantified using a custom-built pipeline using CellProfiler software. The concentration was estimated taking into account the volume of the sample applied to the glass slide and the number of fields of view within the area of the coverslip.

RCP Quantification Using a Sample Analysis Device

Figure 4:
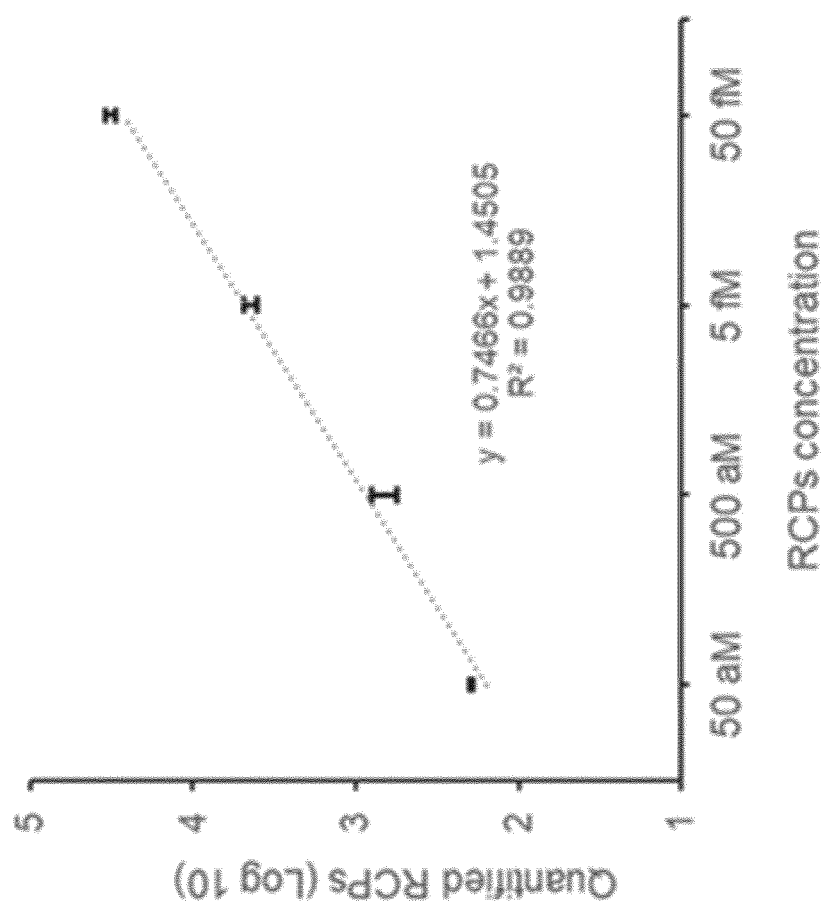
FIG. 4. Graph illustrating quantification of serial dilutions of RCPs using an embodiment of the sample analysis device.
Figure 5:
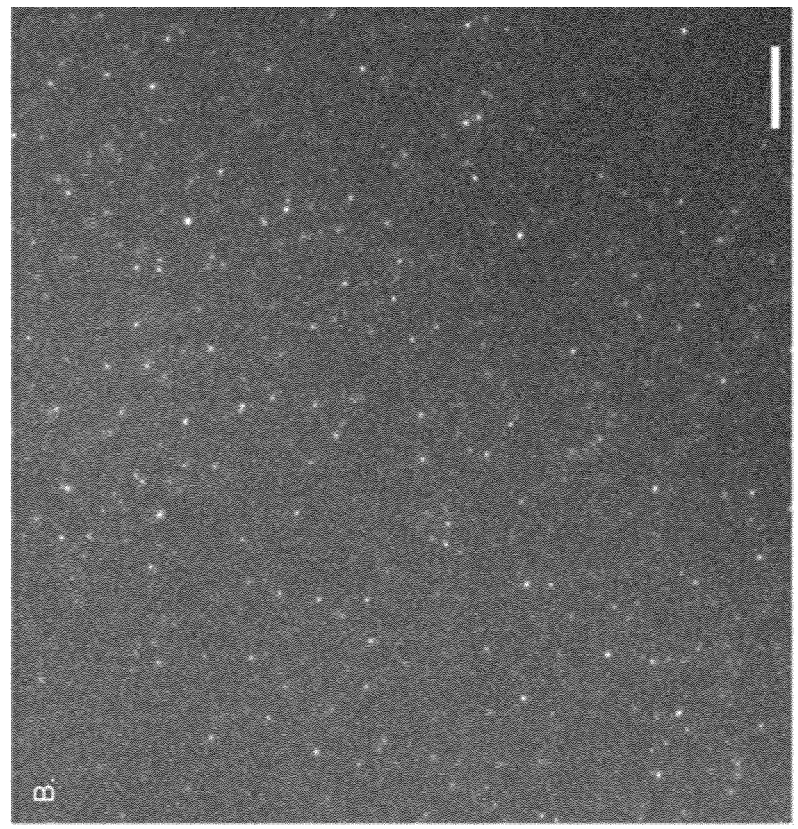
FIG. 5. Picture of fluorescently labeled RCPs immobilized within the sample receiving well of an embodiment of the sample analysis device. A. Sample receiving well imaged with a 10× microscope objective. Scale bar=100 µm. B. Insert zoom of the dotted square in A. showing the RCPs immobilized on the filter membrane. Scale bar=25 µm.
Figure 5:
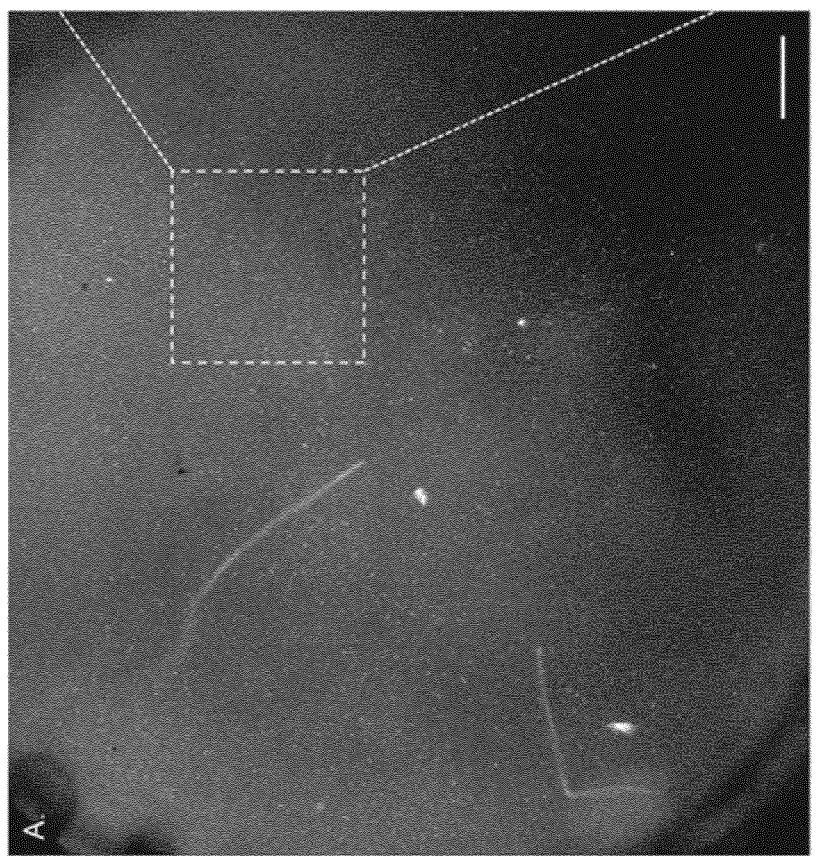

Labelled dilutions of RCPs were applied onto the sample receiving wells embedded in the sample analysis device with a diameter of 1.5 mm. 20 µl of the RCP dilutions were applied onto the sample receiving wells. The applied liquid samples were let to form a large droplet on top of the sample receiving wells. After approximately 4 min, all the liquid sample had been wicked through the filter membrane, after which 5 µl of SlowFade™ Gold Antifade mounting media (ThermoFisher) was applied on top of the sample receiving well and a 13 mm round Menzel Glaser coverslip (VWR) was put on. The sample receiving wells were imaged with a Zeiss Axio Imager Z2 epifluorescence microscope with a 20× magnification objective with a field of view of 0.75×0.75 μm. Resulting RCPs were quantified using a custom-built pipeline using CellProfiler software. This procedure was performed for four dilutions of RCPs in duplicates. FIG. 4 illustrates the number of quantified RCPs on the sample analysis device with the different calculated RCP concentrations of the serial dilutions used in this example. FIG. 5 shows an image of the total area of the sample receiving well captured with a single field of view of a 10× microscope objective (1.3 mm×1.33 mm) after applying a dilution of 5 fM RCPs.

Example 2

Figure 7:
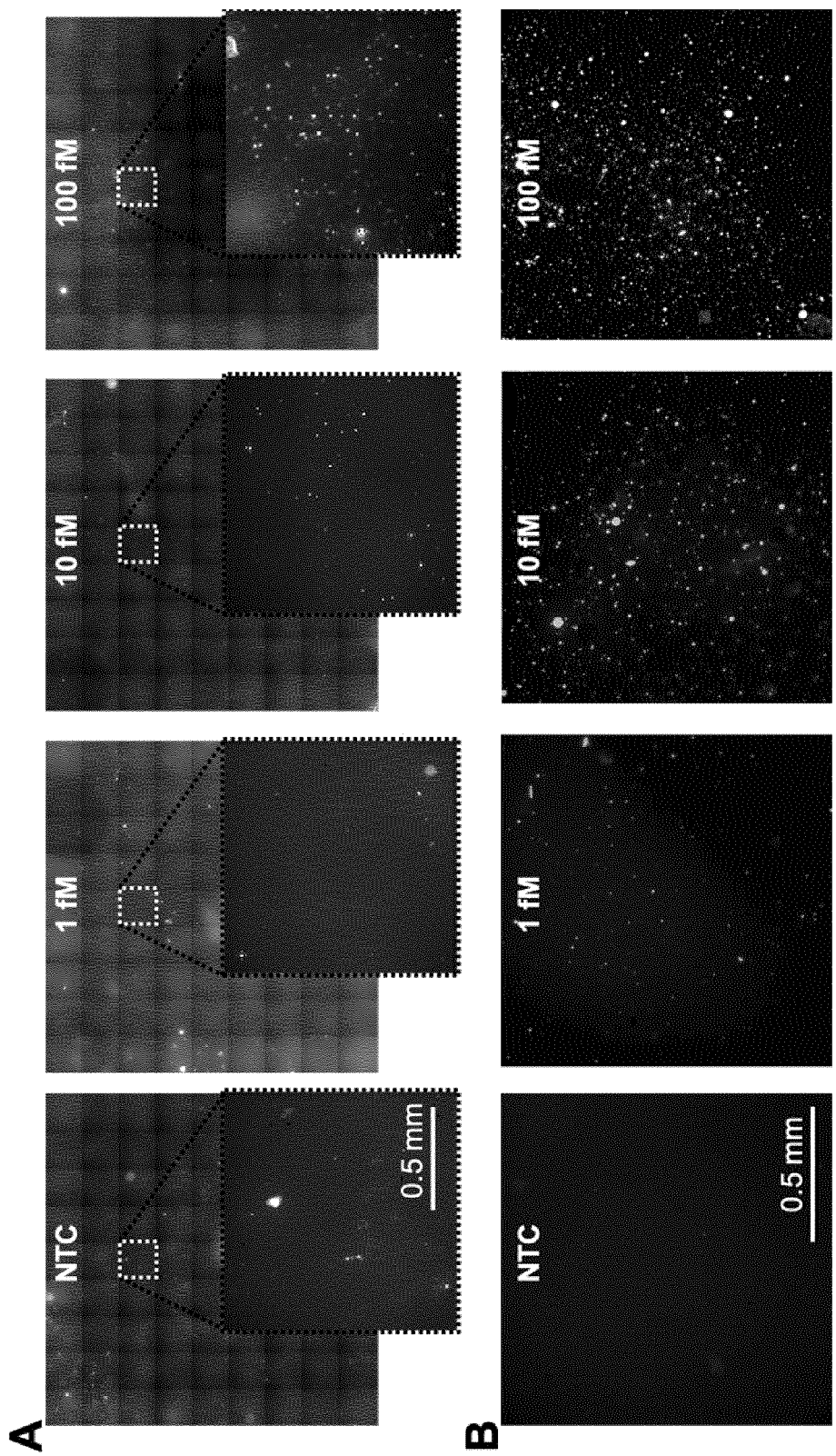
FIG. 7. Shows the comparison of the method of the invention using two membrane sizes and acquiring only one microscopic imaging field of view. One 6×6 mm membrane (FIG. 7A) and the other one 2 mm in diameter (FIG. 7B).

RCA products were prepared the same way as described in the Example 1 and two membrane sizes were used for comparison in the enrichment step. In short, circles were amplified into RCA products for 2 h, 1:10 serial diluted in labelling buffer and labelled with a fluorescent probe. The results of this analysis can be seen in FIG. 7.

For the enrichment, two membrane sizes were prepared. One a 6×6 mm membrane (FIG. 7A) and the other one 2 mm in diameter (FIG. 7B). The membranes were placed on an absorbent pad and 20 μL of RCPs pipetted on them. After the RCP containing solution was enriched, they were placed on a microscope glass slide, with a drop of mounting media being added and it being covered with a cover slip.

The images were acquired under an epifluorescence microscope using a 20× objective. For the large membrane (A) tiling was used while only a single image was acquired for the small circular membrane (B).

The benefits of using the smaller, confined membrane area are:
- The applied sample solution gets equally absorbed and RCPs are distributed homogenously, while the RCPs are heterogeneously distributed on a large membrane as a result from an unequal liquid absorbance (see 100 fM)
- The sensitivity seems to be improved for lower (clinically relevant) RCP concentrations as the background signal (e.g. from buffer/assay or bio-sample components) is reduced.
- Bending of the membrane surface is reduced as smaller surface area results in a more rigid membrane and thus, a reliable enrichment device; especially for circular membranes.

Example 3

Figure 8:
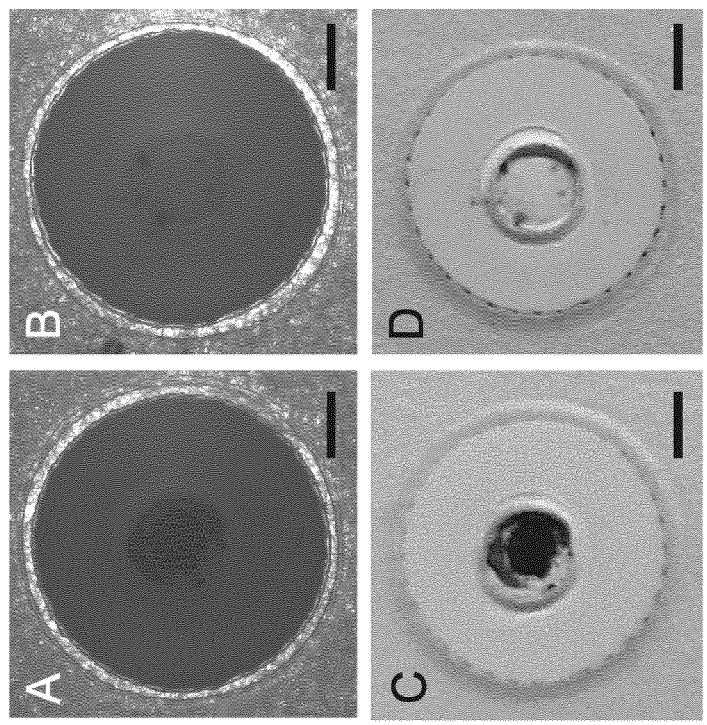
FIG. 8. Shows the results of colorimetric labelling and detection of RCPs on an exemplary device. Microscopic brightfield images of A) 10 nM RCPs and B) no template control. C and D are smartphone photographs of A and B, respectively. The scale bar=1 mm.

The RCA analysis was run as described above in Example 1, but instead of labelling with a fluorophore a substrate was added that would get converted by the DNA-zymatic acitivity of the RCA products and generate a color. After amplification, the RCPs were enriched on the membrane, washed twice with a washing buffer before adding TMB as the substrate. After 5 min the images depicted in FIG. 8 were acquired with a microscope using brightfield and with a smartphone camera. Here is shown the visualization/labelling of RCPs on the membrane based on a simple colorimetric reaction.

The generated color strength is dependent on the RCP concentration and amplification time.

The padlock probe, contained a DNAzyme sequence that resemblances a peroxidase activity upon amplification into an RCP.

RCPs Production for Membrane Performance Comparison

The RCPs were prepared as described above. In short, padlock probes were first circularized together with the synthetic target (SEQ ID NO: 1 & 2), amplified with a 2 h RCA reaction and diluted to 100 fM, 10 fM and 1 fM in the labelling reaction.

RCPs Production for Colorimetric Detection

The padlock probes were circularized in a ligation reaction together with their single-stranded DNA synthetic target. The padlock probe ($PO_4$-TGCTTTGTTTCAGGTGTACTCAGTAATAGTGTCTTA CCCCACCCACCCACCCTCTACACCTTTTTT AGGA, SEQ ID NO: 3) was targeting the same region from the *Staphylococcus aureus* gene (synthetic target, SEQ ID NO:2), used for the fluorescent quantification. Instead of a hybridization site for labelling by fluorescent probes, the padlock probe contained a DNAzyme sequence mimicking that of a peroxidase. For the ligation reaction 15 nM padlock probes, 30 nM synthetic target, T4 ligase reaction buffer (66 mM Tris-HCl (pH 7.5), 10 mM DTT, 10 mM $MgCl_2$, Blirt S.A), 0.2 μg/μl BSA, 0.68 mM ATP (Blirt S.A) and 0.4 U T4 ligase (Blirt S.A) in a final volume of 20 μl. The mixture was incubated at 37° C. for 15 min followed by 65° C. for 2 min. Next, 10 μL of RCA reaction mixture was added containing 0.2 μg/μl BSA, φ29 polymerase reaction buffer (33 mM Tris-acetate pH-7.9, 10 mM Mg-acetate, 66 mM K-acetate, 0.1% (v/v) Tween 20, 1 mM DTT), 125 μM dNTPs (Blirt S.A), 20 μM hemin (Sigma-Aldrich) and 0.4 U/μl φ29 polymerase (Monserrate) was used to amplify the above-mentioned dilution of circles. The RCA reaction was incubated at 37° C. for 2 h and 65° C. for 2 min.

Colorimetric Reaction of RCPs

RCPs were applied onto the sample receiving wells embedded in the sample analysis device with a diameter of 1.5 mm. 20 μl of the RCP dilutions were applied onto the sample receiving wells. The applied liquid samples were let to form a large droplet on top of the sample receiving wells. After approximately 4 min, all the liquid sample had been wicked through the filter membrane. Next, the RCPs were washed with 0.1% Tween-20 in PBS by applying 5 μL twice before adding 10 μL of 3,3',5,5'-Tetramethylbenzidine (TMB; Sigma-Aldrich). The DNAzymatic reaction was incubated for 10 min to allow for the blue color to develop before acquiring the images with a mobile phone camera and a microscope.

Preparation of Different-Sized Membranes for Comparison

The two different-sized membranes were prepared by cutting out a 6×6 mm piece and punching out a 2 mm in diameter membrane of the membrane described in Sample analysis device. To have an equal comparison, the membranes were both placed on an absorbent paper and 20 μl of the RCP concentration applied. Subsequently, 20 μl or 5 μl of SlowFade™ Gold Antifade mounting media (ThermoFisher) was applied on top of the membranes and a 25×25 mm or 13 mm round Menzel Glaser coverslip (VWR) was put on; depending on the membrane size used.

RCP Quantification on Different-Sized Membranes

The different RCP concentrations were quantified as described above in RCP quantification using a sample analysis device for the 2 mm membrane. For the 6×6 mm membrane, images were acquired using a 9×9 tiles under a 20× objective. The Zeiss Axio Imager Z2 epifluorescence microscope with a 20× magnification objective corresponding to a field of view of 0.65×0.65 μm was used for quantification.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

wherein the sample receiving well is defined in the filter membrane or is in liquid connection with the filter membrane;

a liquid-impermeable layer connected to the filter membrane and comprising a through hole, the through hole defining the area of the sample receiving well; and an absorption layer or stack of multiple absorption layers in liquid connection with the filter membrane and configured to suck liquid from the liquid sample received in the sample receiving well through the filter membrane by capillary force; and a spacer layer sandwiched between the liquid-impermeable layer and the absorption layer, wherein the spacer

---

---

The invention claimed is:

1. A sample analysis device comprising:

a sample receiving well or multiple sample receiving wells configured to receive a liquid sample comprising rolling circle amplification (RCA) products (RCPs), the sample receiving well having an area that is no larger than a field of detection area of an optical sensing device, and wherein the area of the sample receiving well has a diameter of 0.5 μm to 9 mm;

a filter membrane or a stack of multiple filter membranes permeable for liquid of the liquid sample but substantially impermeable for RCPs in the liquid sample, layer comprises a through hole configured to house the filter membrane and wherein the spacer layer is liquid-impermeable.

2. The sample analysis device according to claim 1, wherein the filter membrane is a hydrophilic filter membrane comprising hydrophobic barriers extending through a thickness of the filter membrane, the hydrophobic barriers defining the sample receiving well depth in the filter membrane.

3. The sample analysis device according to claim 1, wherein
the liquid-impermeable layer comprises multiple through holes forming multiple sample receiving wells; and
the sample analysis device comprises: multiple filter membranes; and one absorption layer or one stack of multiple absorption layers.

4. The sample analysis device according to claim 1, wherein the absorption layer is configured to suck liquid from the liquid sample received in the sample receiving well through the filter membrane by capillary force and retain the liquid within the absorption layer.

5. The sample analysis device according to claim 1, wherein the sample receiving well has a diameter of from 0.5 μm to 5 mm.

6. A sample analysis system comprising:
an optical sensing device having a field of view; and
a sample analysis device according to claim 1.

7. A sample analysis method comprising:
applying a liquid sample comprising rolling circle amplification (RCA) products (RCPs) into a sample receiving well of a sample analysis device according to claim 1;
filtrating the liquid sample through a filter membrane of the sample analysis device by sucking, by capillary force, liquid from the liquid sample through the filter membrane and into an absorption layer of the sample analysis device; and
determining the amount of RCPs captured in an area of the filter membrane corresponding to the sample receiving well using an optical sensing device.

* * * * *

SEQUENCE LISTING

<160> NUMBER OF SEQ ID NOS: 3

<210> SEQ ID NO 1
<211> LENGTH: 88
<212> TYPE: DNA
<213> ORGANISM: artificial
<220> FEATURE:
<223> OTHER INFORMATION: Padlock Probe with 5'PO4

<400> SEQUENCE: 1
tgctttgttt caggtgtagt gtatgcagct cctcagtaat agtgtcttag tcggaagtac      60
tactctcttc tctacacctt ttttagga                                        88

<210> SEQ ID NO 2
<211> LENGTH: 90
<212> TYPE: DNA
<213> ORGANISM: artificial
<220> FEATURE:
<223> OTHER INFORMATION: Synthetic Target

<400> SEQUENCE: 2
ttaaattaat gtacaaaggt caaccaatga cattcagact attattggtt gatacacctg      60
aaacaaagca tcctaaaaaa ggtgtagaga                                      90

<210> SEQ ID NO 3
<211> LENGTH: 27
<212> TYPE: DNA
<213> ORGANISM: artificial
<220> FEATURE:
<223> OTHER INFORMATION: 5' Cyanine 3-Tag

<400> SEQUENCE: 3
cytcctcagt aatagtgtct tactttt                                         27